US005484384A

United States Patent [19]
Fearnot

[11] Patent Number: 5,484,384
[45] Date of Patent: Jan. 16, 1996

[54] MINIMALLY INVASIVE MEDICAL DEVICE FOR PROVIDING A RADIATION TREATMENT

[75] Inventor: Neal E. Fearnot, West Lafayette, Ind.

[73] Assignee: MED Institute, Inc., West Lafayette, Ind.

[21] Appl. No.: 321,106

[22] Filed: Oct. 11, 1994

Related U.S. Application Data

[63] Continuation-in-part of Ser. No. 647,280, Jan. 29, 1991, Pat. No. 5,354,257.

[51] Int. Cl.$^6$ ..................................................... A61N 5/00
[52] U.S. Cl. ........................................................... 600/3
[58] Field of Search ........................... 600/3, 7; 128/657, 128/658, 653.4–654, 656

[56] References Cited

U.S. PATENT DOCUMENTS

| | | | |
|---|---|---|---|
| 2,546,761 | 3/1951 | Loftus | 128/1.2 |
| 4,244,357 | 1/1981 | Morrison | 128/1.2 |
| 4,554,929 | 11/1985 | Samson et al. | 128/772 |
| 4,819,618 | 4/1989 | Liprie | 600/3 |
| 5,001,825 | 3/1991 | Halpern | 128/772 |
| 5,059,166 | 10/1991 | Fischell et al. | 600/3 |
| 5,135,503 | 8/1992 | Abrams | 604/164 |
| 5,213,561 | 5/1993 | Weinstein et al. | 600/7 |
| 5,302,168 | 4/1994 | Hess | 600/3 |
| 5,411,466 | 5/1995 | Hess | 600/3 |

FOREIGN PATENT DOCUMENTS

| | | | |
|---|---|---|---|
| 2348715 | 11/1977 | France. | |
| 2203650 | 10/1988 | United Kingdom | 128/772 |
| 9200776 | 1/1992 | WIPO | 600/7 |

OTHER PUBLICATIONS

"Wire Guides", *Cook Diagnostic Interventional Products for Radiology, Cardiology and Surgery*, Cook Incorporated, Bloomington, Ind., 1986, pp. 3, 6, and 18.

"Stone Removal", *Cook Diagnostic Interventional Products for Radiology, Cardiology, and Surgery*, Cook Incorporated, Bloomington, Ind., 1986, pp. 1, 3, and 5.

"Intravascular Retrieval", *Cook Diagnostic Interventional Products for Radiology, Cardiology, and Surgery*, Cook Incorporated, Bloomington, Ind., 1986, p. 3.

*Primary Examiner*—Angela D. Sykes
*Assistant Examiner*—Eric F. Winakur
*Attorney, Agent, or Firm*—Richard J. Godlewski

[57] ABSTRACT

A minimally invasive medical device (10, 23, 31, 40, 41, 46, 49) for providing a selected and controlled radiation dosage to the vascular system of a patient. The device includes an outer sheath (15) with an inner elongated member (55) slidably disposed in the passage (59) of the outer sheath. The inner elongated member has an expandable distal portion (11) of spring wires (12, 13) looped about a distal end 14 of the inner elongated member. The inner elongated member also includes a proximal portion (17) extending from the proximal end (58) of the outer sheath for extending and withdrawing the expandable distal portion from the distal end (56) of the outer sheath. The spring wires of the expandable distal portion include a radiation source (18) alloyed with or disposed around the spring wires. The inner elongated member also alternatively includes a catheter (60) with an inflatable balloon (38) forming the expandable distal portion thereof.

17 Claims, 4 Drawing Sheets

5,484,384

MINIMALLY INVASIVE MEDICAL DEVICE FOR PROVIDING A RADIATION TREATMENT

CROSS-REFERENCE TO RELATED APPLICATIONS

This application is a continuation-in-part application of application Ser. No. 07/647,280, filed Jan. 29, 1991, now U.S. Pat. No. 5,354,257, and is incorporated herein by reference.

TECHNICAL FIELD

This invention relates to minimally invasive medical devices anti, in particular, a minimally invasive medical device having an expandable distal portion for providing a radiation treatment in a body passageway or vessel.

BACKGROUND OF THE INVENTION

Occlusion of the coronary arteries can decrease blood flow to the extent that a myocardium infarction occurs. This typically occurs due to cholesterol or plaque depositing on the vessel walls and subsequently building up to occlude the vessel. As a result, several minimally invasive procedures such as balloon angioplasty or laser ablation are utilized to reopen or enlarge the lumen of the vessel. A problem with these procedures is that abrasion or dissection of the vessel wall may occur during the therapeutic procedure to reopen or enlarge the lumen of the vessel. As a result, thrombi formation and occlusion of the vessel lumen may also occur.

In addition to balloon angioplasty or laser ablation procedures, a coronary stent is typically positioned in the treated vessel to maintain the patency of the vessel. A problem with the use of a stent is that smooth muscle proliferates or intimal hyperplasia occurs in response to the presence of the stent in the vessel. As a result, restenosis of the vessel typically occurs within a period of six months.

An approach to decreasing smooth muscle proliferation or intimal hyperplasia is the use of a stent with a radioisotope source for irradiating tissue at the stent site. The radioisotope source is contained in the surface coating of the stent or contained in the metal alloy that forms the stent. In use, the stent is embedded into the plaque on a blood vessel wall. A problem with the use of this radioactive stent is that the stent is a permanent implant in the blood vessel. As a result, smooth muscle proliferation or intimal hyperplasia may occur in response to the presence of the stent in the vessel over the entire life of a patient, causing chronic restenosis of the vessel. A limitation of the use of this stent is that the radiation exposure to the stent site is controlled by the half-life of the radioisotope. Once implanted, the radiation dosage of the stent cannot be increased or decreased in response to the changing needs of the patient. Not only are these problems associated with the coronary vessels but are applicable to other parts of the vascular system, such as the occlusion of the femoral or iliac vessels.

SUMMARY OF THE INVENTION

The foregoing problems are solved and a technical advance is achieved in an illustrative minimally invasive medical device for providing a radiation treatment in a body passageway such as a vessel in the vascular system. The preferred minimally invasive medical device includes an outer sheath with an inner elongated member having an expandable distal portion slidably disposed in the passage of the outer sheath. The expandable distal portion also includes a radiation source for advantageously providing a controlled radiation treatment to a blood vessel.

The expandable distal portion includes spring wires looped about a distal end of the inner elongated member for expanding and contacting the wall of the blood vessel when extended from the distal end of the outer sheath. The radiation source comprises a radioactive material such as iridium and the like, which in the preferred embodiment is combined with the spring wires to form radioactive metal alloy spring wires. In another aspect, the radiation source forms a radioactive surface coating or layer disposed on the outer surface of the spring wires. In yet another aspect, the radiation source comprises radioactive material sleeves attached to the spring wires.

In another aspect of the invention, the medical device includes a wire guide extendable through the distal portion of the expandable spring wire basket. To advantageously affect a greater mass of radioactive material, the spring wires are helically shaped. The medical device also includes a coil extending distally from and rotatable with respect to the spring wire basket. To minimize trauma to the vessel wall, the coil has a distal end with a greater flexibility than that of the proximal end and further includes a tapered mandril positioned longitudinally within the coil.

In yet another aspect of the invention, the inner elongated member includes a catheter with the expandable distal portion including an inflatable balloon. Advantageously, the radiation source comprises a radioactive fluid for inflating the balloon and treating the affected blood vessel. A second lumen is also included in the catheter for blood to perfuse therethrough.

Figure 1:
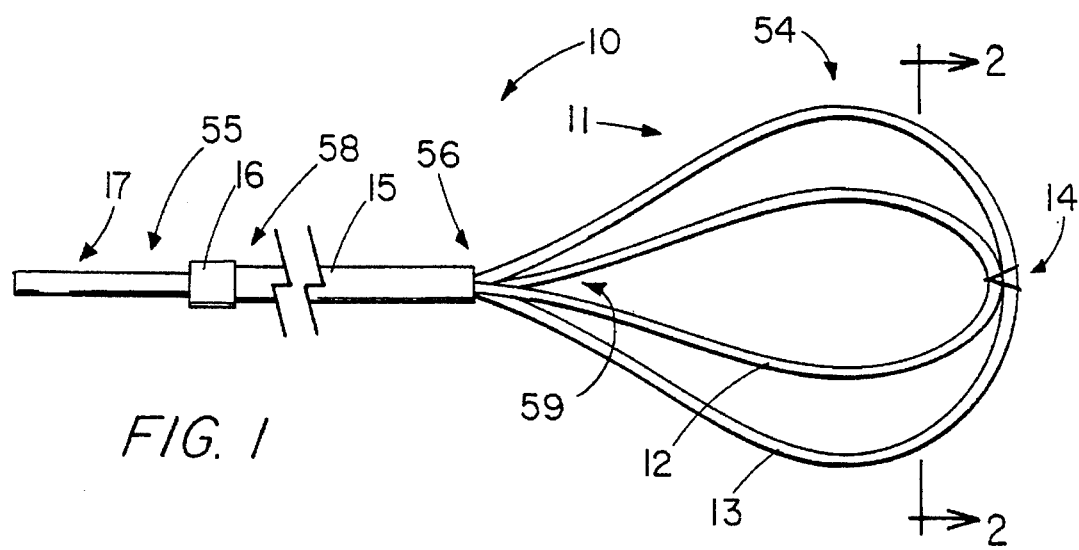
FIG. 1 depicts a preferred embodiment of the minimally invasive medical device of the present invention.

Depicted in FIG. 1 is a preferred embodiment of a minimally invasive medical device 10 including an expandable wire basket 54, for providing a selective and controlled radiation treatment in a body passageway. This minimally invasive medical device has particular application as a percutaneously inserted intravascular device for controllably providing a therapeutic radiation dosage to an affected area of a coronary vessel that is deemed likely to experience restenosis. Restenosis typically occurs after a procedure to open or enlarge the vessel, such as balloon angioplasty, laser ablation, or stent placement.

Figure 8:
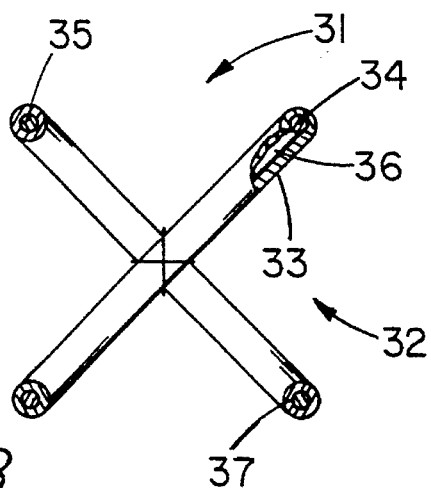
FIG. 8 depicts still another aspect of the medical device of FIG. 1.

Device 10 includes an outer sheath 15 with inner elongated member 55, which is longitudinally and slidably disposed through passage 59 of the outer sheath. Inner elongated member includes an expandable distal portion 11 such as expandable wire basket 54, which in an expanded condition extends from distal end 56 of the outer sheath. The stranded wire basket is formed from commercially available spring wires 12 and 13 of, for example, stainless steel, platinum or tantalum, that are looped about distal end 14 of the inner elongated member. Device 10 further includes a radiation source 18 such as commercially available radioactive material, for example, iridium, which is combined with spring wires 12 and 13 to form radioactive metal alloy spring wires. Alternatively, a commercially available radioactive material surface coating 33 or outer layer is disposed about outer surfaces 36 and 37 of respective spring wires 34 and 35, as depicted in FIG. 8. Spring wires 12 and 13 extend proximally from the expandable wire basket portion through end cap 16 and outer sheath 15, which is formed from a commercially available polytetrafluoroethylene tube. Proximal end 17 of the inner elongated member or spring wires provides a convenient grip or handle for extending and withdrawing the expandable wire basket from and into the outer sheath.

Figure 2:
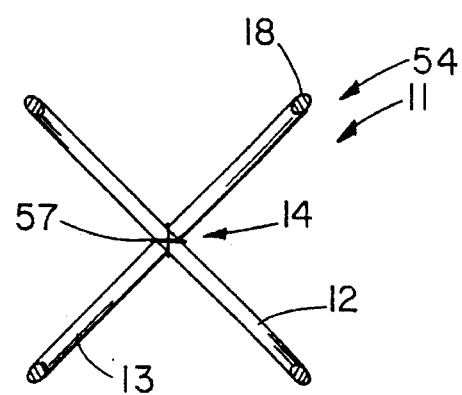
FIG. 2 depicts an enlarged cross-sectional view of the medical device of FIG. 1 taken along the line 2—2.

FIG. 2 depicts an enlarged cross-sectional view of expanded wire basket 54 of FIG. 1 taken along the line 2—2. Spring wires 12 and 13 are looped at distal end 14 of the inner elongated member and affixed to one another using, for example, suture material 57 or a suitable medical grade adhesive. In the preferred embodiment, radiation source 18 is commercially available iridium which has been alloyed with stainless steel to form spring wires 12 and 13.

Device 10 somewhat resembles the Burhenne-Hawkins Stone Basket commercially available from Cook Incorporated, Bloomington, Ind. However, device 10 has been modified for introduction into the vascular system of a patient and is, for example, approximately 95 cm in length and 8 French (2.7 mm or 0.105") in diameter when the expandable distal portion is collapsed and retracted within the outer sheath. Expandable distal portion 11 is approximately 7 mm long and 3 mm in diameter when extended from the sheath to assume an open, expanded condition that allows the device to center itself in the vessel lumen. To accommodate coronary arteries, the maximum outside diameter of the expandable distal portion when in a fully expanded condition preferably falls in a range of 0.5 to 4.0 mm. However, the lengths and diameters of device 10 and expandable distal portion 11 can be adjusted to accommodate large or small blood vessels or any other body passageways desired to be irradiated.

Figure 3:
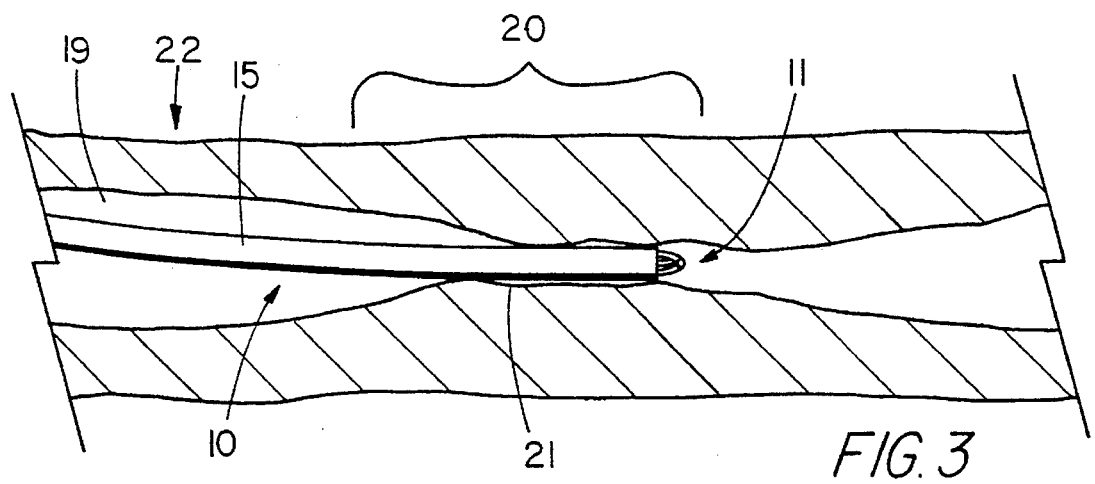
FIG. 3 depicts the medical device of FIG. 1 positioned in a coronary artery.
Figure 4:
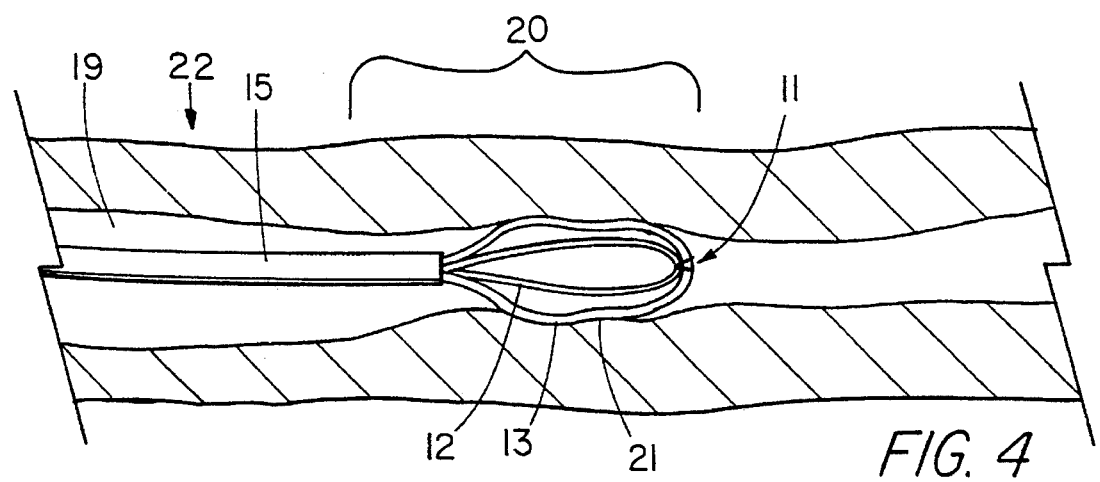
FIG. 4 depicts the medical device of FIG. 3 with the outer sheath thereof pulled back.
Figure 5:
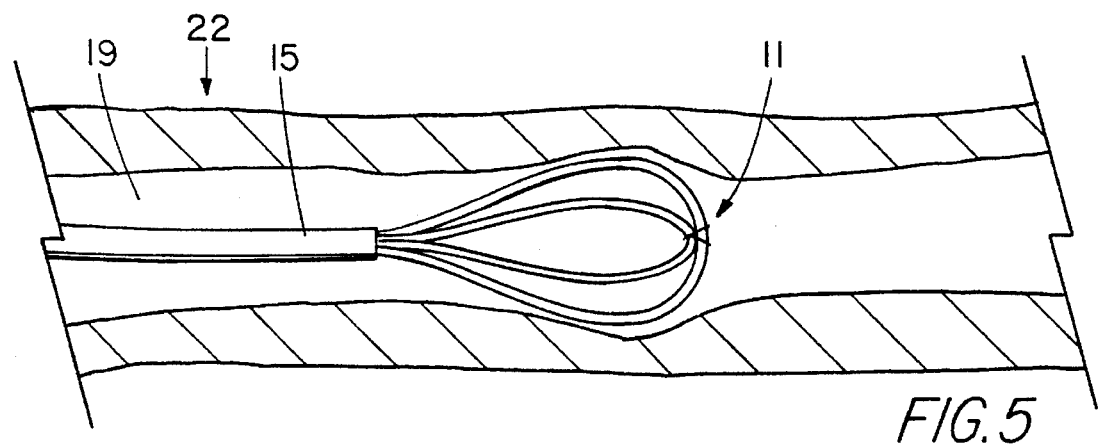
FIG. 5 depicts a coronary artery with the medical device of FIG. 3 therein after a short-term localized radiation treatment.

FIGS. 3–5 depict coronary artery 22 with artery lumen 19 partially occluded by intimal hyperplasia and smooth muscle cell proliferation at vessel region or treatment site 20. FIG. 3 depicts device 10 positioned in the lumen of the coronary artery with expandable distal basket portion 11 in the partially occluded treatment site for providing short-term, localized irradiation of the coronary artery wall. When sheath 15 is pulled proximally as depicted in FIG. 4, expandable distal basket portion 11 extends therefrom and opens to an expanded condition. Spring wires 12 and 13, which include a radioactive metal alloy, atraumatically rest against the inner surface, or intimal layer, of coronary artery wall 21 and the proliferation of cells thereon. As a result, the spring wires are positioned away from the center of the artery lumen for minimizing the interruption of blood flow therethrough.

FIG. 5 depicts artery 22 after a short-term, localized radiation treatment with lumen 19 widened about the treatment site. The spring wires of the expandable basket portion are no longer in contact with the artery wall. To remove device 10 from the coronary artery, sheath 15 is pushed distally over expandable distal basket portion 11 for collapsing the spring wires and containing them in the sheath.

Figure 6:
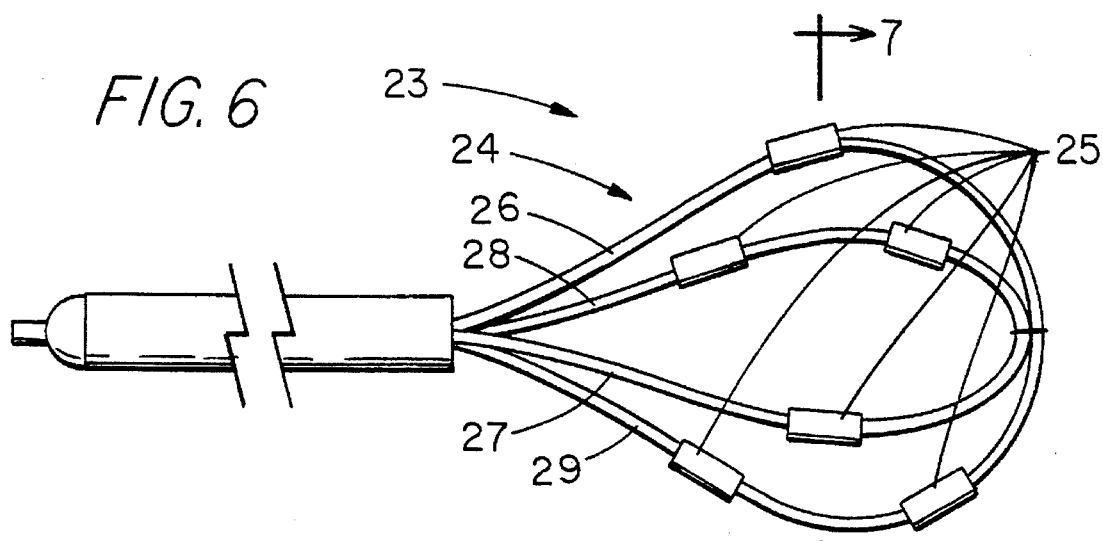
FIG. 6 depicts another aspect of a medical device of FIG. 1.
Figure 7:
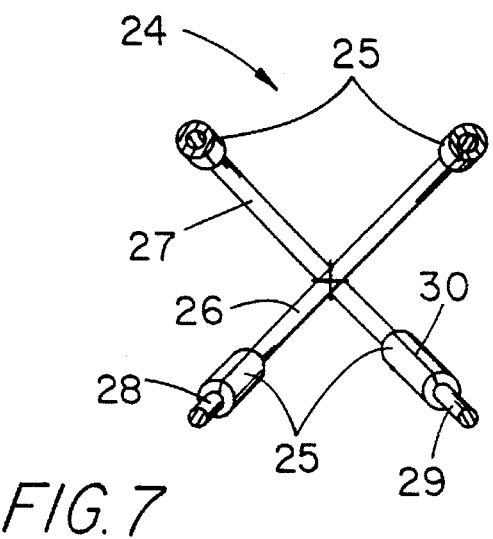
FIG. 7 is an enlarged cross-sectional view of the medical device of FIG. 6 taken along the line 7—7.

FIG. 6 depicts a minimally invasive medical device 23, which includes an expandable wire basket 24 similar to device 10 except for the radiation source. The radiation source includes a plurality of commercially available radioactive iridium material tubular sleeves 25 disposed around outer surfaces 26 and 27 of spring wires 28 and 29 using soft solder 30, as depicted in FIG. 7. FIG. 7 is an enlarged cross-sectional view of expandable basket 24 of FIG. 6 taken along the line 7—7. Alternatively, the plurality of radioactive material tubular sleeves 25 is affixed about the outer surface of the spring wires by crimping.

FIG. 8 depicts minimally invasive medical device 31, which includes expandable distal basket portion 32 and the radiation source in the form of a radioactive surface coating 33 or a radioactive outer layer disposed on outer surfaces 36 and 37 of respective spring wires 34 and 35. The surface coating includes a plastic material with radioactive iridium particles dispersed throughout. The outer layer includes radioactive iridium plated on the spring wires.

Figure 9:
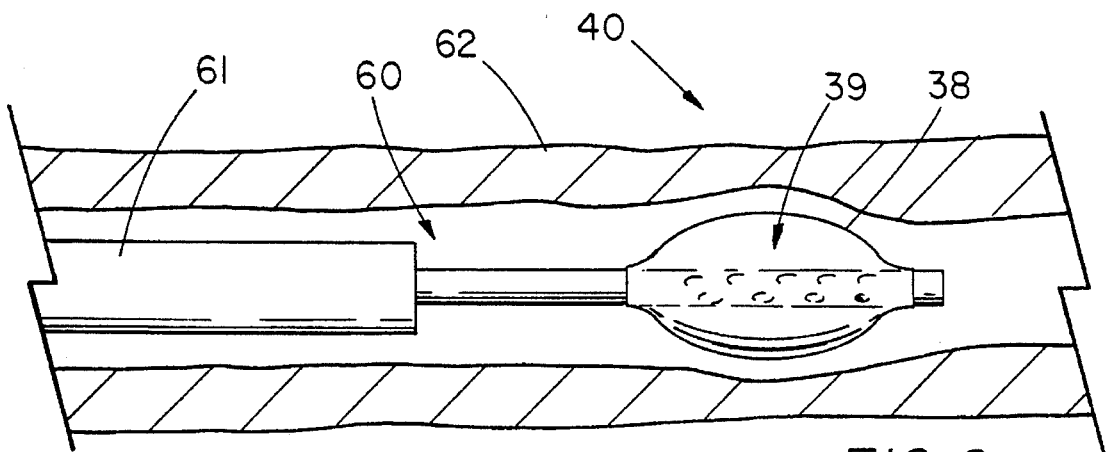
FIG. 9 depicts yet another aspect of the medical device of FIG. 1.

FIG. 9 depicts minimally invasive medical device 40, which represents another aspect of the invention. The inner elongated member of this alternative embodiment includes a dual lumen balloon catheter 60 distally extended from outer sheath 61. The balloon catheter includes an expandable distal portion such as an inflatable balloon 38 for expanding and atraumatically contacting blood vessel wall 62 about a treatment site. The balloon provides for centering the device in a blood vessel lumen. One lumen of the catheter provides for inflating the balloon with radioactive fluid 39, and another lumen allows blood perfusion through the catheter to the portion of the blood vessel lumen on the other side of the expanded balloon. The radiation source of this device such as radioactive fluid 39 is injected into the balloon for irradiating the treatment site.

Figure 10:
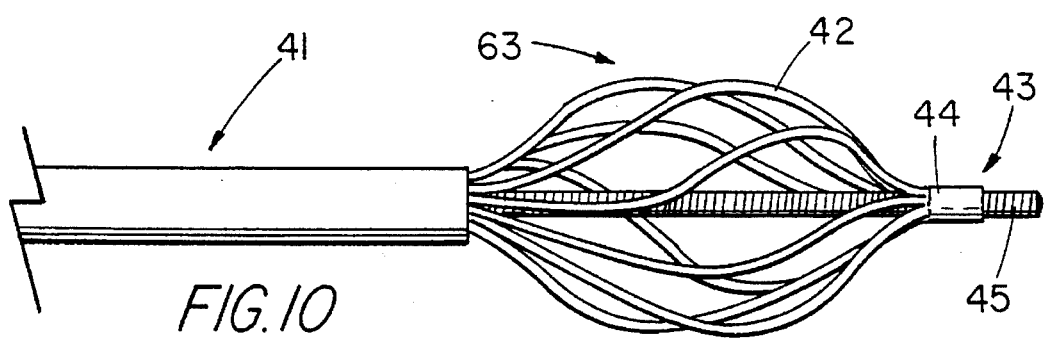
FIG. 10 depicts still yet another aspect of the medical device of FIG. 1.

FIG. 10 depicts a minimally invasive medical device 41, which represents yet another embodiment of the invention. Device 41 includes a plurality (eight) of interweaved spring wires 42 attached about distal end 43 of the inner elongated member by soft solder 44. A wire guide 45 is depicted extending through device 41 for facilitating advancement of the device through the vascular system and to the treatment site of a patient. Device 41 somewhat resembles the eight wire basket used for nonoperative removal of stones from the biliary tract that is commercially available from Cook Incorporated, Bloomington, Ind.

Figure 11:
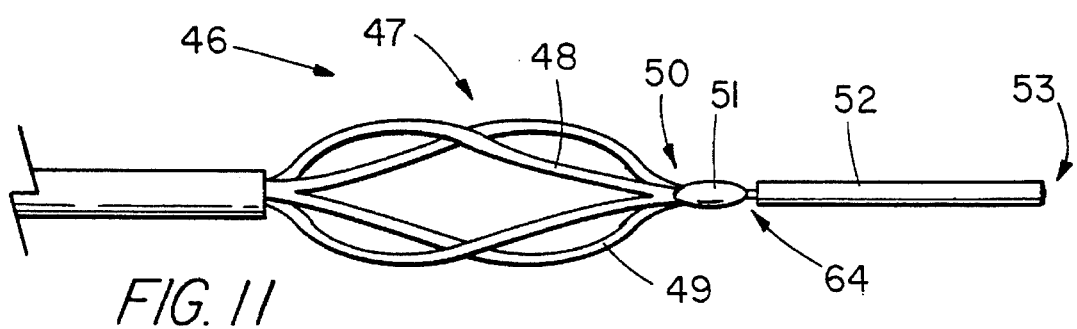
FIG. 11 depicts another embodiment of the present invention.

FIG. 11 depicts minimally invasive medical device 46, which represents yet another embodiment of the invention. The device includes expandable wire basket portion 47 and radiation source 48 in the form of a surface coating or an outer layer disposed thereon. Expandable distal portion 47 includes a plurality (four) of helically positioned wires 49 attached about distal end 50 using, for example, soft solder. Device 46 somewhat resembles the Dotter Intravascular Retriever Basket that is commercially available from Cook Incorporated, Bloomington, Ind. Device 46 further includes well-known swivel connection 51 extending between the plurality of four helical wires 49 and flexible wire guide coil 52. The flexible coil provides a deflectable, atraumatic means for maintaining the position of the wire basket in a body passageway during a therapeutic procedure. The flexible wire guide coil is positioned over a tapered mandril or, alternatively, a straight length of round wire and a safety wire, so that flexible wire guide coil 52 exhibits a gradual increase in flexibility toward distal end 53 thereof. Swivel connection 51 provides for the rotation of expandable basket portion 46 while flexible coil 52 remains stationary. Swivel connection 51 of device 46 somewhat resembles the Swivel Connection of the Schwarz Biliary Stone Removal Basket that is commercially available from Cook Incorporated, Bloomington, Ind.

It is to be understood that the above-described minimally invasive intravascular medical device for providing a radiation treatment in a body passageway is merely an illustrative embodiment of the principles of this invention and that other devices, instruments, or apparatuses may be devised by those skilled in the art without departing from the spirit and scope of this invention. In particular, it is contemplated that a radioactive material other than an iridium material may be used as a radiation source. It is further contemplated that many commercially available radially expandable medical devices such as wire baskets may be modified to attach a radiation source about the expandable portion thereof for providing a radiation treatment to a body passageway and, in particular, preventing intimal hyperplasia and smooth muscle proliferation which causes stenosis or restenosis of a blood vessel passageway. Although described as being particularly applicable to the vascular system using well-known percutaneous insertion techniques, it is contemplated that the minimally invasive device is applicable for providing treatment to the pulmonary system as well as the gastrointestinal tract. Treatment of the biliary and urinary system are also contemplated with expandable medical devices such as wire baskets, particularly adapted with the radiation source for treating the particular anatomical system.

What is claimed is:

1. A minimally invasive medical device for providing a radiation treatment, comprising:
    an outer sheath having a distal end, a proximal end, and a passage extending longitudinally therein; and
    an inner elongated member having an expandable distal portion and a proximal portion that is slidably disposed in said passage of said outer sheath, said proximal portion having a proximal end extending from said proximal end of said outer sheath and movable with respect to said proximal end of said outer sheath for extending said expandable distal portion from said distal end of said outer sheath, said expandable distal portion biased to an expanded condition when extended from said distal end of said outer sheath, said expandable distal portion also including a radiation source.

2. The medical device of claim 1 wherein said expandable distal portion includes an expandable wire basket.

3. The medical device of claim 2 further including a wire guide extendable through said expandable distal portion.

4. The medical device of claim 1 wherein said expandable distal portion includes a first spring wire and a second spring wire looped about a distal end of said inner elongated member.

5. The medical device of claim 4 wherein said radiation source comprises a radioactive material and wherein said radioactive material and said spring wires are combined to form radioactive metal alloy spring wires.

6. The medical device of claim 4 wherein said radiation source comprises a radioactive surface coating.

7. The medical device of claim 4 wherein said radiation source comprises a radioactive material sleeve disposed around said spring wires.

8. The medical device of claim 4 wherein said spring wires are helically shaped.

9. The medical device of claim 8 further comprising a coil extending distally from and rotatably connected to said spring wires.

10. The medical device of claim 9 wherein said coil has a proximal end and a distal end with greater flexibility than that of said proximal end of said coil.

11. The medical device of claim 10 wherein said coil includes a tapered mandril positioned in said coil.

12. A minimally invasive medical device for providing a radiation treatment, comprising:
    an outer sheath having a distal end, a proximal end, and a passage extending longitudinally therein;
    a basket having a first spring wire and a second spring wire, said basket being positionable in said passage of said outer sheath, being in a collapsed condition when positioned in said passage of said outer sheath, and being in an expanded condition when extended from said distal end of said outer sheath; and
    a radiation source disposed about said spring wires.

13. The medical device of claim 12 wherein said radiation source and said first and second wires are combined to form first and second radioactive metal alloy wires.

14. The medical device of claim 12 wherein said radiation source comprises a radioactive material surface coating on said spring wires.

15. The medical device of claim 12 wherein said radiation source comprises a layer of radioactive material on said spring wires.

16. The medical device of claim 12 wherein said radiation source comprises tubular sleeves disposed on said spring wires.

17. A minimally invasive medical device for providing a radiation treatment, comprising:
    an outer polytetrafluoroethylene sheath having a distal end, a proximal end, and a passage extending longitudinally therein;
    a basket having a first stainless steel spring wire and a second stainless steel spring wire, said basket being positionable in said passage of said outer sheath, being in a collapsed condition when positioned in said outer sheath, and being in an expanded condition when extended from said distal end of said outer sheath, said first and said second stainless steel spring wires extending through and having a proximal end extending from said proximal end of said outer sheath, said proximal end of said first and said second stainless steel spring wires being movable for slidably positioning said basket in and out of said passage of said outer sheath; and
    an iridium material combined with said first and said second stainless steel spring wires to form a first and a second radioactive metal alloy spring wire.

* * * * *